United States Patent [19]
Johnson

[11] Patent Number: 5,420,223
[45] Date of Patent: May 30, 1995

[54] CURING AGENTS/ACCELERATORS, CURABLE COMPOSITIONS AND PROCESSES

[75] Inventor: John R. Johnson, Danville, Ind.

[73] Assignee: Reilly Industries, Inc., Indianapolis, Ind.

[21] Appl. No.: 138,895

[22] Filed: Oct. 19, 1993

Related U.S. Application Data

[63] Continuation of Ser. No. 853,809, Mar. 19, 1992, abandoned, which is a continuation of Ser. No. 825,005, Jan. 24, 1992, abandoned.

[51] Int. Cl.$^6$ .......................................... C08G 65/10
[52] U.S. Cl. ............................... 528/91; 528/93; 528/94; 525/117; 523/400
[58] Field of Search ............... 502/155, 162, 167, 200, 502/203, 231, 354; 528/91, 93, 94, 110; 525/108, 117; 523/400

[56] References Cited

U.S. PATENT DOCUMENTS

| | | | |
|---|---|---|---|
| 2,824,083 | 2/1958 | Parry et al. | 528/91 |
| 2,839,495 | 6/1958 | Carey | 528/91 |
| 2,909,494 | 10/1959 | Parry et al. | 528/91 |
| 3,519,604 | 7/1970 | Maurer | 528/94 |
| 4,614,788 | 9/1986 | Dettlofl et al. | 528/91 |
| 4,731,370 | 3/1988 | Watanabe et al. | 546/279 |
| 4,816,500 | 3/1989 | Corcoran | 523/400 |
| 4,871,806 | 10/1989 | Shalati et al. | 525/108 |

FOREIGN PATENT DOCUMENTS

| | | |
|---|---|---|
| 0316874 | 5/1989 | European Pat. Off. . |
| 0411927 | 2/1991 | European Pat. Off. . |

OTHER PUBLICATIONS

CAS Registry File No.: 80965-30-6.

*Primary Examiner*—John Kight, III
*Assistant Examiner*—Richard Jones
*Attorney, Agent, or Firm*—Woodard, Emhardt, Naughton, Moriarty & McNett

[57] ABSTRACT

Described are several preferred acid salts and complexes of N,N-dimethylpyridine (DMAP) and 4-(4-methyl-1-piperidinyl)pyridine (MPP) which are useful as curing agents or as accelerators in preferred epoxy resin curing processes. Also described are particularly preferred processes for forming cured epoxy resin materials which are advantageously employed in large production line scale operations, and curable coating compositions.

16 Claims, 1 Drawing Sheet

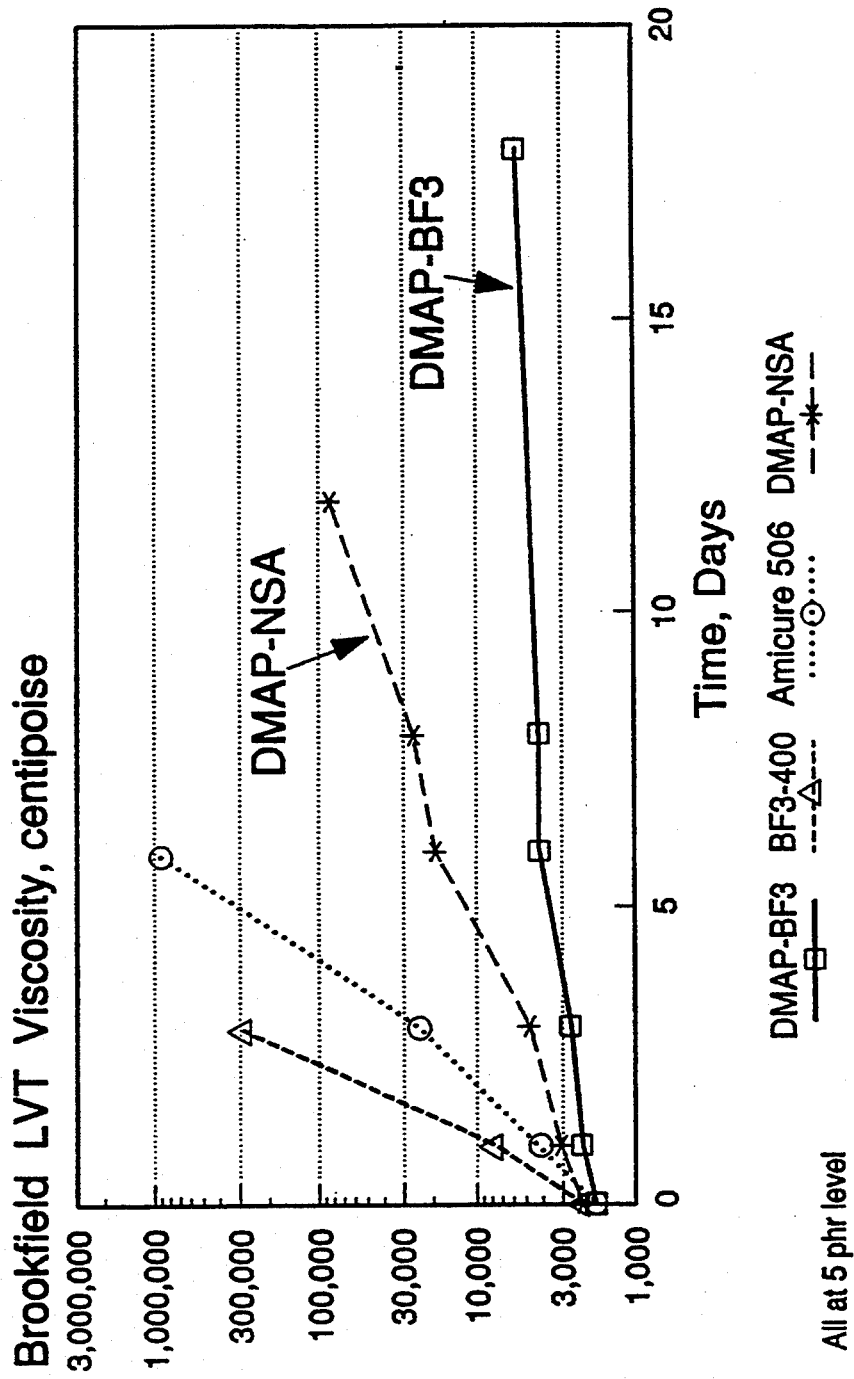

CURING AGENTS/ACCELERATORS, CURABLE COMPOSITIONS AND PROCESSES

This application is a continuation of application Ser. No. 07/853,809, filed Mar. 19, 1992, now abandoned, which is a continuation of application Ser. No. 07/825,005, filed Jan. 24, 1992, now abandoned.

The present invention relates generally to the field of curable compositions for coatings, adhesives and the like. More particularly, one aspect of this invention relates to novel epoxy resin curing accelerators and agents exhibiting latent catalysis and to one component epoxy resin formulations containing them. Other aspects of this invention relate to a process for forming a cured epoxy resin material that can be advantageously applied to production line-scale operations, and to certain curable compositions and their curing.

The term "epoxy resin," as generally used in the art, refers to any molecule containing two or more epoxy groups. This technology had its genesis in research conducted in the United States and Europe just prior to World War II, and the interest in and production of epoxy resin has continued to grow since that time. Epoxy resins have proven to be enormously versatile compounds, and accordingly are used in thousands of industrial applications including adhesives, body solders, caulking compounds, casting compounds, sealants, potting and encapsulation compounds, and laminating resins. Epoxy-based solution and powder coatings are used as maintenance and product finishes, marine finishes, masonry finishes, structural steel coatings, tank coatings, aircraft finishes, automotive primers, can and drum linings, and collapsible-tube coatings, etc. For a further and more in-depth discussion of epoxy resin technology from its beginnings, reference can be made to H. Lee and K. Neville, *Handbook of Epoxy Resins*, New York, McGraw Hill (1967). Many other publications are also available including numerous patents which can provide additional background relating to work in the area. See, e.g., U.S. Pat. Nos. 3,004,952, 2,909,494, 2,717,885, and 2,839,495, and English Patent Nos. 955,748, 955,873, 956,044, and 963,058.

The most valuable single property of epoxy resins is their ability to transform readily from the liquid (or thermoplastic) state to tough, hard thermoset solids upon mixing with a suitable curing agent (also referred to as a hardener, activator, or catalyst). It is often necessary to heat the resulting mixture in order to effect this transformation depending upon the precise epoxy resin and curing agent used.

Lewis acid-amine complexes represent one general class of epoxy resin curing agents. (See C. A. May and Y. Tanaka, *Epoxy Resins Chemistry and Technology*, Marcel Dekker Inc., N.Y. 1973, p. 293). Various Lewis acid-amine complexes have shown to be effective as latent epoxy resin hardeners for use in prepreg laminates, casting compounds, or the like involving heat-cure type applications. Desirably, such complexes exhibit "latent catalysis." This term refers to the capacity of the curing agent to remain in an inactive state until initiated, usually accomplished by heating to dissociate the inactive complex and free the curing species.

Suitable amines for the formation of epoxy resin curing Lewis acid complexes have included-some primary and secondary amines. For example, monoethylamine boron trifluoride has been used commercially as an epoxy curing agent, as have benzylamine-BF$_3$, piperidine-BF$_3$, and a number of analine-BF$_3$ derivatives.

Tertiary amines have also been identified as having the ability to cure epoxy resins, see e.g. H. Lee and K. Neville, *Handbook of Epoxy Resins*, New York, McGraw Hill (1967) and M. P. Stevens, *Polymer Chemistry—An Introduction;* Addison-Wesley: Massachusetts, 1975, although they are less often encountered perhaps because in many cases they have demonstrated very high activation temperatures and therefore have unacceptable cure properties at curing temperatures advantageously used in industry. For example, the heat-cure activation temperatures for the primary and secondary derivatives noted above are around 130° C. and 170° C., respectively, while it is as high as 225° C. for pyridine.

Despite extensive research in acadamia and industry there remains a need for epoxy resin and other curing agents and curing accelerators having the unique properties of very high latency and acceptable activation temperatures and curing times for advantageous use, and for imp, roved one component curable compositions including epoxy resin formulations and methods for curing epoxies. The present invention addresses these needs.

SUMMARY OF THE INVENTION

One preferred embodiment of tile present invention provides a 4-(4-methyl-1-piperidinyl)pyridine or 4-(N,N-dimethylamino)pyridine salt or complex selected from the group consisting of:
  4-(N,N-dimethylamino)pyridine-p-toluenesulfonic acid addition salt;
  4-(N,N-dimethylamino)pyridine-1-naphthalenesulfonic acid addition salt;
  4-(4-methyl-1-piperidinyl)pyridine-p-toluenesulfonic acid addition salt;
  4-(4-methyl-1-piperidinyl)pyridine-1-naphthalenesulfonic acid addition salt; and
  4-(4-methyl-1-piperidinyl)pyridine-boron trifluoride complex.

These novel materials are useful as epoxy resin curing agents, or as curing accelerators when used together with other curing agents.

Another preferred embodiment of the present invention provides a latent one component heat-curable epoxy resin formulation comprising epoxy resin and one or more of the above-identified salts or complexes. The salt or complex can be present as curing agent or as accelerator in combination with another curing agent such as dicyandiamide, acid anhydride, adipic dihydrazide, etc. Further related embodiments provide processes for curing epoxy resins, and epoxy curing compositions in which the novel salts or complexes are employed. Another preferred embodiment of the present invention relates to a particularly preferred process for forming a cured epoxy resin material at advantageous temperatures and cure times suitable for a production line scale operation. This process comprises heating an epoxy resin having blended therein a curing agent and as accelerator about 1 to 8 parts by weight of 4-(N,N-dimethylamino)pyridine-boron trifluoride complex per 100 parts by weight of epoxy resin at a temperature of about 100° to 150° C. and for a period of about 5 to 90 minutes.

Another preferred embodiment of the invention provides a heat-curable coating composition, comprising: (i) a compound having anhydride functionality; (ii) a compound having epoxy or hydroxyl functionality; with the proviso that at least one of (i) or (ii) has acrylic functionality; and (iii) as a crosslinking catalyst, 4-(N,N-dimethylamino)pyridine-boron trifluoride complex. Such acrylic-containing coating compositions enjoy preferred status in industries such as the auto industry, and the incorporation of the DMAP-BF$_3$ complex provides important advantages as hereinafter further discussed.

Another embodiment of the invention provides a powdered coating composition.

The present invention thus provides both novel salts and complexes useful in the curing of epoxy and other resins, as well as highly preferred and advantageous epoxy resin curing processes including those applicable to rapid, commercial scale production line operations. Curable coating compositions and their curing processes are also provided, and further objects and advantages of the invention Hill be apparent from the following description.

BRIEF DESCRIPTION OF THE FIGURE

FIG. 1 is a graph depicting viscosity build over time at 25° C. for epoxy systems containing DMAP-naphthalene sulfonic acid salt and DMAP-BF$_3$ complex accelerators, as compared to similar epoxy systems containing two commercially available accelerators.

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As mentioned above, one preferred embodiment of the present invention relates to novel acid addition salts or boron trifluoride complexes of the pyridine derivatives, 4-(N,N-dimethylamino)pyridine (DMAP) and 4-(4-methyl-1-piperidinyl)pyridine (MPP), which are useful as epoxy resin curing agents (i.e. when used as the sole or primary hardener) or as accelerators when used together with other curing agents. These acid addition salts and complexes may be prepared by dissolving and mixing the selected acid or complexing agent and pyridine derivative together in an appropriate organic solvent. This may be done by dissolving one of the components in an organic solvent and then slowly adding the other component, either neat or in solvent, under appropriate conditions. Where boron trifluoride complexes are involved, BF$_3$ etherate may be slowly added to a solution of the pyridine derivative preferably under an inert atmosphere such as nitrogen. The components are usually mixed together, for instance by stirring, for at least one hour. The solid acid addition salt or complex thus formed can be conventionally recovered and purified by recrystallization or other means.

Suitable solvents for the preparation of the acid addition salts and the complexes include inert organic solvents such as aliphatic and aromatic hydrocarbons, for instance hexane, benzene or toluene, ethers such as tetrahydrofuran or diethyl ether, alcohols such as butanol, etc. Additional suitable solvents will be apparent to those ordinarily skilled in the area.

Using this general procedure, the following acid addition salts and BF$_3$ complexes were prepared, found to be stable at room temperature, and identified by $^1$H NMR, FTIR and elemental analysis:
4-(N,N-dimethylamino)pyridine-p-toluenesulfonic acid salt;
4-(N,N-dimethylamino)pyridine-1-naphthalenesulfonic acid salt;
4-(N,N-dimethylamino)pyridine-boron trifluoride complex;
4-(4-methyl-1-piperidinyl)pyridine-p-toluenesulfonic acid salt;
4-(4-methyl-1-piperidinyl)pyridine-1-naphthalenesulfonic acid salt;
4-(4-methyl-1-piperidinyl)pyridine-boron trifluoride complex.

Once prepared, the acid addition salt or the complex can be blended with the epoxy resin and used as the sole or primary curing agent, or may be used as an accelerator (i.e. to provide faster cure rates at lower temperatures) when blended into the epoxy resin along with another curing agent or hardener at typical levels known in the art.

When the complex or salt is used as an accelerator, the curing agent may be any of those conventionally employed. These include for example, curing agents such as phenol-novolac, cresol-novolac and 3,3'-diallyl-4,4'-dihydroxybisphenol A; amine compounds such as 4,4'-methylenebis(2-ethylaniline), 4'4-methylenebis(2,6-diethylaniline) and 4,4'-methylenebis(2-ethyl-6-methylaniline); acid anhydrides such as Nadic Methyl Anhydride (methyl-bicyclo[2.2.1]heptene-2,3-dicarboxylic anhydride), phthalic anhydride, tetrahydrophthalic anhydride, methyltetrahydrophthalic anhydride, trimellitic anhydride, and pyromellitic anhydride; amide compounds such as dicyandiamide; and dihydrazide compounds such as adipic dihydrazide and isophthalic dihydrazide. These may be included in the usual amounts. When used as an accelerator, the salt or complex of the present invention and the curing agent are generally included in effective amounts to cure the epoxy resin when heated. More desirably the salt or complex as accelerator is included in the range of about 1 to 8 parts per 100 parts epoxy resin. In particularly preferred formulations, the salt or complex is used together with a dicyandiamide, acid anhydride or adipic dihydrazide curing agent.

The one component epoxy resin formulation thus prepared can be cured by heating so as to cause the formulation to convert to a hard thermoset solid. Generally, the temperature of the curing step may range from 70° C. up to the decomposition temperature of the formulation, and will often fall in the range of about 100° to 150° C.

As indicated above, another preferred embodiment provides a process for forming a cured epoxy resin material at highly advantageous temperatures and cure times in a production line scale operation. As further background in this area, a problem encountered with latent curing accelerators or agents is that typically their latency and the cure temperatures and times required with their use are directly related. That is, materials which are very highly latent, if useful at all as curing agents or accelerators, usually require curing at high temperatures and for long durations. While such a combination may be useful for some applications, it is not advantageous for large scale production line operations as are commonly encountered in the auto body industry, for example. In these high volume industries cure temperatures are desirably maintained at about 100° to 150° C. to avoid excessive energy costs, and it is important that cure times of less than about 90 minutes be possible to allow for highly advantageous large scale production lines. Until now, curing accelerators and agents which meet these curing specifications have sacrificed high latency.

The latency/(curing temperature and duration) dichotomy can be illustrated by observing the ratio of the gel times provided by a curing accelerator at lower and higher temperatures. More desirable curing accelerators will exhibit higher ratios in this regard, which reflect high latency up until curing temperatures are reached, and subsequent rapid catalysis. It has now been discovered that the $BF_3$ complex of 4-(N,N-dimethylamino)pyridine exhibits an unexpected and extraordinarily high low temperature/high temperature gel time ratio which enables its use in curing processes advantageous for production line scale operations as discussed above even though it exhibits extraordinary latency. For example, in Example 7 below the 4-(N,N-dimethylamino)pyridine-boron trifluoride complex as accelerator exhibited a 70° C./120° C. gel time ratio of about 40.1, whereas in similar runs this gel time ratio for BF3-400, a commercially available curing accelerator, was about 27.4 (see Table 1). Similarly, the 100° C./150° C. gel time ratio for a one component epoxy resin/dicyandiamide adhesive formulation including 4-(N,N-dimethylamino)pyridine-boron trifluoride complex as accelerator was greater than 63, whereas the best commercial accelerator tested in the same system exhibited a ratio of only about 26 (see Table 2). Accordingly, another preferred embodiment of the present invention relates to a process for forming a cured epoxy resin material at highly advantageous temperatures and cure times suitable for use in a production line scale operation, comprising heating an epoxy resin having blended therein a curing agent and as accelerator about 1 to 8 parts by weight of 4-(N,N-dimethylamino)pyridine-boron trifluoride complex per 100 parts of epoxy resin at a temperature of about 100° to 150° C. and for a period of about 5 to 90 minutes.

Still another embodiment of the invention relates to a heat-curable coating compositions comprising: (i) a compound having anhydride functionality; (ii) a compound having epoxy or hydroxyl functionality; with the proviso that at least one of (i) or (ii) has acrylic functionality; and (iii) as a crosslinking catalyst, 4-(N,N-dimethylamino)pyridine-boron trifluoride complex. Curable compositions having components (i) and (ii) have have gained preferred status in the automotive and similar industries as paints, coatings, laminates and the like, and the incorporation of (iii) into such compositions is found to provide highly improved compositions possessing unexpected and advantageous properties. For example, incorporation of the DMAP-$BF_3$ complex provides compositions having excellent latency/activity characteristics which form hard, durable coatings. Further, these compositions have good colour, with no substantial darkening appearing prior to curing or in the cured coating.

Further preferred components these curing compositions are generally known to the art and literature. For instance, further preferred components as set forth below may be drawn from U.S. Pat. Nos. 4,816,500 and 4,871,806, European Patent Application No. 88119031.8 filed Nov. 15, 1988 (published May 24, 1989, EP 0316874), and European Patent Application No. 90308471.3 filed Aug. 1, 1990 (published Feb. 6, 1991, EP O411927), each hereby incorporated herein by reference.

The anhydride-functional compound may be a polymer or copolymer having a weight average molecular weight of less than 100,000 and containing at least two reactive anhydride groups. Low molecular weight monomeric anhydrides may also be used.

Anhydride copolymers can be prepared, for example, from one or more of the monomers of styrene, methacrylate, or acrylates with one or more of the monomers of itaconic acid, itaconic anhydride, maleic anhydride or isobutenyl succinic anhydride. (After formation of the polymer the itaconic acid which is contained in the polymer is converted to the anhydride). As those skilled in the art will appreciate, there are a number of other monomers which could also be used in forming the anhydride-functional copolymer. For instance, some of these monomers are disclosed in U.S. Pat. No. 4,816,500.

The epoxy resin of the coatings may be any polymer, copolymer or compound with a weight average molecular weight of less than 100,000 containing at least two epoxy groups. Low molecular weight monomeric epoxies may also be used. The epoxy components may be copolymers prepared from alkyl (meth)acrylates with glycidyl (meth)acrylates (as used herein (meth)acrylates refers to either acrylates or methacrylates). These preferred polymers may be used by themselves or in combination with the polyglycidyethers or sorbitol. Other useful epoxies are Araldite CY-184® (from Ciba-Geigy Corporation) and epoxies based on Bisphenol A such as Epon 1001® (available from Shell Chemical Company). As will be apparent to one skilled in the art there are a number of different monomers which could also be used to form an epoxy polymer. Some of these are also disclosed in U.S. Pat. No. 4,816,500.

Hydroxyl containing compounds which can be used are polymers or copolymers containing hydroxy functionality with a weight average molecular weight of less than 100,000 containing at least two hydroxy groups. Low molecular weight monomeric hydroxyl compounds may also be used. Hydroxyl compounds which are copolymers containing alkyl (meth)acrylates and hydroxy functional (meth)acrylates have been found desirable in the art. Also, hydroxy functional polyesters can be used.

As indicated above, in accordance with this embodiment, at least one of the above components will contain the acrylic functionality.

The composition of this embodiment may also include an acid functional compound. The acid functional compounds that may be used are monomeric, oligomeric, or polymeric which may or may not contain hydroxyl functionality. If polymeric, the compounds are typically formed by polymerizing monomers of alkyl (meth)acrylates where the alkyl groups have 1-12 carbon atoms and ethylenically unsaturated acids. Optionally, the acid functional polymer can also contain other components such as styrene, acrylonitrile, methacrylontrile in amounts of about 0.1-50% by weight.

The coating composition formed using the components described above may contain about 20% to about 80% of the component having at least two epoxy groups. The coating composition may also contain components such as monomeric anhydrides, acid functional monomeric, oligomeric or polymeric components which may or may not contain hydroxyl functionality (if there are acid functional groups present there must also be epoxy groups present in order to get cure); hydroxy functional polymers; and self-stabilized dispersed resins. Examples of monomeric anhydrides are methyl hexahydrophthalic anhydride and the like. Examples of such acid functional components are glycolic acid and acrylate/methacrylic acid copolymer and the like.

Typical solvents used to prepare acrylic-anhydride copolymers, and used as a diluent for the coating composition include toluene, xylene, butyl acetate, ethylbenzene, higher boiling aromatic hydrocarbons, amyl acetate, ethyl acetate, propyl acetate, ethylene or propylene glycol mono alkyl ether acetates and the like.

Generally, the composition is applied by conventional techniques such as spraying and electrostatic spraying. The resulting coating is cured at elevated temperatures, preferably about 80° to about 165° C., more preferably about 80° to about 130° C. The coating can be applied in pigmented or non-pigmented (clear) form. Coatings are applied to form a finish about 0.5–5 mils thick, and preferably 1–2 mils thick.

To improve weatherability of the clear finish of the coating composition, about 0.1–5%, by weight, based on the weight of the binder, of an ultraviolet light stabilizer or a combination of ultraviolet light stabilizers can be added. These stabilizers include ultraviolet light absorbers, screeners, quenchers and specific hindered amine light stabilizers. Also, about 0.1–5% by weight, based on the weight of the binder, of an antioxidant can be added.

Generally, when the coating composition of this invention is used as a clear coating, it is applied by conventional spraying techniques to a color or base coat of a vehicle such as an automobile or truck. The coatings are baked so as to develop a proper cure. In refinishing automobiles and trucks, the clear coating is applied to a color coat and then can be baked to form a clear finish. The resulting clear coat or finish is about 1–5 mils thick, preferably 1–2 mils thick.

The composition can be pigmented to form a colored finish or primer. About 0.1–200% by weight based on the weight of the binder, of conventional pigments can be added using conventional techniques in which a mill based containing pigment, dispersant and solvent is first formed. The mil based is then mixed with the composition to form a colored composition. This composition can be applied and cured as shown above.

To promote a further understanding of the invention and its preferred embodiments and advantages, the following practical examples are provided. It will be understood, however, that these examples are illustrative, and not limiting of the invention. In these examples, generally, toluene (commercial grade) was distilled before use. The sodium salt of 1-naphthalenesulfonic acid (Aldrich, tech. grade, 80%) was protonated with HCl in 2-butanol and washed repeatedly with a saturated aqueous NaCl solution before use. All other chemicals were used with no purification: 2-butanol, Chem Central, commercial grade; 98%; N-N-dimethyl-4-pyridinamine, Reilly Industries, Inc., Indianapolis, Ind., ethyl acetate, Aldrich, 99.5+%; methanol, commercial grade; 4-(4-methyl-piperidinyl)pyridine, Reilly Industries, Inc.; phenol, Aldrich 99+%; sodium chloride, Aldrich, 98+%; tetrahydrofuran, Aldrich, 99.5+%; p-toluenesulfonic acid monohydrate, Aldrich 99%; water, distilled.

Analysis of salts was conducted on a Varian 60 MHz $^1$H NMR spectrometer. Melting points were obtained on a MEL-TEMP melting point apparatus, 50/60 cycles, 110–120 Volts–200 Watts. FTIR analysis was conducted on a Nicolet 510P FTIR with a 552 spectrophotometer and a Perkin-Elmer 561 recorder. Elemental analyses were conducted by an independent testing laboratory. Unless otherwise indicated, parts and ratios are given in terms of weight.

EXAMPLE 1 p-Toluenesulfonic Acid Salt of DMAP

A 2 L beaker equipped with a thermometer and a mechanical stirrer was charged with 95.1 g p-toluenesulfonic acid monohydrate (0.50 mol) and 500 mL toluene. The slurry was stirred and heated to 50° C. to achieve dissolution. The solution was cooled to 30° C. and a 55° C. solution of 61.1 g (0.50 mol) DMAP in 250 mL toluene was slowly added with stirring, giving a white precipitate immediately. The temperature of the reaction reached 45° C. After stirring 2 hours, the slurry was filtered and the solids dried until nearly dry (156.2 g). These white solids were charged into a 1L flask equipped with condenser with drying tube, thermometer, stirrer, and Dean-Stark trap. Toluene (500 mL) was added, and H$_2$O was removed via azeotropic distillation. The dried slurry was filtered, giving 174.9 g wet solids. These solids were recrystallized from THF (approx. 1L), filtered and dried. Dry weight=141.6 g. Analysis of $^1$H NMR and FTIR verified the structure as that of the p-toluenesulfonic acid salt of DMAP; mp—175°–176° C.; NaOH titration=101.07%; FW=294.38 g/mol; soluble in H$_2$O, MeOH, DMSO and acetone. Calculated for $C_{14}H_{18}N_2O_3S$: C, 57.12%; H, 6,16%; N, 9.52%, S, 10–89%; O, 16.31%; Found: C, 57 124%: H, 6.12%; N, 9.54%; S, 11,06%; O, 16.14%.

EXAMPLE 2 p-Toluenesulfonic Acid Salt of MPP

The apparatus used in Example 1 was cleaned and charged with 95.1 g (0.50 mol) p-toluenesulfonic acid monohydrate and 750 mL toluene. The mixture was stirred to aid dissolution. MPP (88.13 g, 0.50 mol) was added slowly over 2 min. The reaction reached 38° C. The slurry was stirred for 1.5 hours, filtered, and the white solids allowed to air dry until partially dry (173.6 g). The solids were recrystallized from THF (approx. 1 L), filtered and dried. Dry weight=1782.1 g. Analysis by $^1$H NMR and FTIR verified the structure as that of the p-toluenesulfonic acid salt of MPP; mp=149°–150° C.; NaOH titration=108.83%; FW=348.48.g/mol; soluble in H$_2$O, MeOH. DMSO and acetone. Calculated for $C_{18}H_{24}N_2O_3S$: C, 62.4%; H, 6.94%; N, 8.04%; S, 9.20%; O, 13.77%; Found: C, 62.075; H, 6.90%; N, 7.98%; S, 9.04%; O, 14.01%.

EXAMPLE 3

1-Naphthalenesulfonic Acid Salt of DMAP

A 2L beaker equipped with a thermometer and a mechanical stirrer was charged with 89.8 g (0.39 mol) sodium salt of 1-naphthalenesulfonic acid, 700 mL 2-butanol, and 350 mL H$_2$O. The mixture was stirred to homogenity, after which 35 mL 37% HCl (0.43 mol) were added. The reaction was stirred 30 min, charged to a separatory funnel and the bottom aqueous layer removed. The organic layer was washed with 100 mL saturated NaCl solution and recharged to the 2L beaker. A solution of 36.7 g (0.30 mol) DMAP in 250 mL 2-butanol was added slowly, and the reaction stirred for 2 hrs. The 2-butanol was removed on a rotary evaporator, and the white solids were allowed to air-dry. The solids were recrystallized from THF, yielding 106.7 g white solids. $^1$H NMR and FTIR verified the structure as that of the 1-naphthalenesulfonic acid salt of DMAP, mp=177°–181° C., NaOH titration=90.67%; 8.1% ash by combustion analysis; FW=330.41 g/mol; soluble in H$_2$O, MeOH, DMSO, and acetone. Calculated for C$_{17}$H$_{18}$N$_2$O$_3$S: C, 61 80%; H, 5.49%; N, 8.48%; S, 9.70%; O, 14.53%. Found: C, 61.03%; H, 5.35%; N, 8.08%, S, 10.69%; O, 14.84%.

EXAMPLE 4

1-Naphthalenesulfonic Acid Salt of MPP

The apparatus used in Example 3 was cleaned and charged with 74.8 g (0.32 mol) sodium salt of 1-naphthalenesulfonic acid, 600 mL 2-butanol and 300 mL H$_2$O. The mixture was stirred to homogeneity, after which 27 mL 37% HCl (0.33 mol) were added. The reaction was stirred 30 min, then extracted and washed with 100 mL saturated NaCl solution as in Example 3. The organic layer was recharged to the 2L beaker, and 44.1 g (0.25 mol) MPP were added slowly. The reaction was stirred for more than 2 hrs. The 2-butanol was removed on a rotary evaporator and the solids allowed to air-dry. The solids were recrystallized from THF, yielding 102.4 g white solids. $^1$H NMR and FTIR verified the structure as that of the 1-naphthalenesulfonic acid salt of MPP; mp=127°–132° C.; NaOH titration=89.85%; 8.1% ash by combustion analysis; FW=384.50 G/mol; soluble in H$_2$O, MeOH DMSO, and acetone. Calculated for C$_{21}$H$_{24}$N$_2$O$_3$S: C, 65.60%; H, 6.29%; N, 7.29%; S, 8.34%; O, 12.48%. Found: C, 64.24%; H, 6.13%; N, 6.82%; S, 8.65%; O, 14.16%.

EXAMPLE 5

DMAP-BF$_3$ Complex

DMAP (50.3 g, 0.412 mole) was dissolved in THF (400 mL). BF$_3$ etherate (58.6 g, 0.413 mole) was added dropwise, under nitrogen, over a 20 minute period. The temperature of tile mixture reached 44° C. whereafter it was stirred for 1.5 hours. A white precipitate formed during the BF$_3$ etherate addition. The mixture was cooled to 5° C. and the product filtered. The product was washed with THF (50 mL) and dried in a vacuum oven (m.p. 140°–146° C.).

EXAMPLE 6

MPP-BF$_3$ Complex

Freshly distilled MPP (70.5 g, 0.4 mol) was charged to a 1500 mL beaker containing 500 mL tetrahydrofuran. The mixture was stirred to homogeneity via magnetic stirring. Boron trifluoride etherate (56.8 g, 0.4 mol) was added slowly at room temperature with vigorous agitation. The exothermic reaction raised the temperature to 45° C. The mixture was stirred until room temperature was again reached (50 min.), and allowed to stand for 5 minutes before transfer to a 2000 mL flask. The solution was evaporated until the product remained in about 50 mL solvent. The white crystalline material was isolated by suction filtration, washing the crystals with 100 mL tetrahydrofuran. The product was air-dried to constant weight, yielding 61.42 g MPP-BF$_3$ complex (63% isolated yield), mp=145°–147° C.

EXAMPLES 7–14

Catalyzed One Component Epoxy Adhesive Formulations Containing Acid Anhydride Curing Agents The acid salts and complexes prepared in the previous examples were dispersed at 2.5 parts (based on active amine equivalent functionality), in 51.3 parts of EPON 828 epoxy resin, having an EEW (epoxy equivalent weight) of 185 to 190, and 46.2 parts of nadic methyl anhydride (NMA) hardener, using a DISPERMAT CV disperser at 2500 rpm for 3 minutes.

Gel times were tested on twenty gram portions of the above mixes in 18 by 150 mm test tubes, using a SUNSHINE gel meter that was equipped with a thermostatically controlled silicone oil bath. The oil bath permitted precise temperature regulation of the test sample to within plus or minus 0.2° C. Gelation is noted in this instrument by measurement of viscosity build during polymerization. At a predetermined viscosity point, a highly reproducible torque is registered by the instrument, i.e., gel point.

Table 1 demonstrates the relative cure latency of these various salts and complexes, as defined by increasing gel time at lower temperatures. The boron trifluoride complex and the p-toluene sulfonic acid ("ptsa") and 1-naphthalenesulfonic acid ("NSA") salts of dimethylaminopyridine are the most latent curatives of this group, followed by AMICURE 506, a commercially available "latent" curing agent. The BF3 complex of dimethylaminopyridine is uniquely latent, as evidenced by its extremely long gel time of 1180 minutes, at 70° C. This is substantially longer than ally of the commercially available catalysts tested, including AMICURE 506 (p-toluenesulfonic acid salt of DBU) and AMICURE SA-1, the phenol salt of DBU (1,8 Diaza(5,4,0-)bicyclo undecene-7). 1-naphthalenesulfonic acid also yields a salt of the dimethylaminopyridine which is highly latent as an epoxy catalyst.

In addition, the 70° C./120° C. gel time ratio of the system containing the boron trifluoride complex dimethylaminopyridine was 40.1, thus highlighting the unexpected nature of its ability to cure quickly and effectively in large scale production-line type operations while also yielding extremely long one component shelf life at ambient temperatures.

TABLE 1

Gel Time of Various "Latent" DMAP & MPP Acid Salts*

| | | Gel Time in Minutes Resin Temperature (°C.) | | | | |
|---|---|---|---|---|---|---|
| Ex. | Acid Salt | 70 | 80 | 90 | 120 | 150 |
| 7 | DMAP-BF3** | 1180 | 434 | 239 | 29.4 | 7.7 |
| 8 | DMAP-NSA | 560 | | 273 | 38.1 | 8.5 |
| 9 | DMAP-ptsa | >1200 | | 357 | 39.8 | |
| 10 | MPP-ptsa | 742 | | 253 | 41.3 | |
| 11 | MPP-BF3 | >1041 | 605.5 | 245 | 26.9 | 8.0 |
| 12 | AMICURE 506 | | | 351 | 100.2 | 29.9 |
| 13 | BF3-400 | 104 | 32 | 23.4 | 3.8 | 2.1 |
| 14 | SA-1 | | | 35 | 6.7 | |

*All contain 5 phr of catalyst +90 phr of NMA
**In additional testing using the same procedure, DMAP-BF$_3$ exhibited gel times of 113.2 and 57.0 minutes at temperatures of 100° and 110° C., respectively.

EXAMPLES 15-18

One Component Epoxy Resin Coating/Adhesive Formulations Containing Latent Catalyst Hardeners The dimethylaminopyridine complex of boron trifluoride and salt of 1-naphthalenesulfonic acid prepared as In addition, MPP-BF$_3$ was evaluated in similar testing except at temperatures of 70° C., 90° C. and 120° C. The respective gel times were >1431 minutes, >1434.1 min. and 137.2 min. These results also demonstrate excellent latency and highly desirable low temperature/high temperature gel time ratios.

TABLE 2

| Ex. | Catalyst (PHR) | Sunshine G.T., min. | | | Brk. RVT Viscosity, cPs(*1000) | | | | |
|---|---|---|---|---|---|---|---|---|---|
| | | 100° C. | 120° C. | 150° C. | Initial | 1 Week | 2 Weeks | 1 Month | 2 Months |
| 19 | DMAP-BF3 (1.5) | 813.2 | 114 | 12.8 | 23.0 | 23.6 | 27.0 | 27.4 | 29.0 |
| 20 | DMAP-NSA (1.5) | 1384 | | 9.6 | | | | | |
| 21 | ANJICURE PN 23 (1.5) | 244.1 | 62.6 | 9.5 | 27.2 | 25.6 | 27.2 | | |
| 22 | CUREZOL 2MA-OK, (1.5) | 145 | 47.4 | 7.9 | 22.6 | 26.0 | 27.6 | | |

*All contain 5 weight parts Dicyandiamide per one hundred weight parts resin (i.e. "5 PHR Dicyandiamide"), and 2.5 PHR fumed silicone in Examples 3 and 5 were dispersed at 5 parts in 100 parts of a general purpose epoxy resin, having an EEW (epoxy equivalent weight) of 85 to 190, using a DISPERMAT CV dispenser at 2500 rpm for 3 minutes or until homogeneous.

Latency at ambient temperature is a prime criterion for true one component catalyzed coatings or adhesives systems. The maintenance of a flat ambient temperature viscosity during storage of these compositions assures adequate workability and a reasonable lifetime of the product on the shelf.

As can be seen in FIG. 1, Brookfield viscosity build at 25° C. is very flat for the boron trifluoride complex of dimethylaminopyridine and moderately flat for the 1-naphthalenesulfonic acid salt version. In contrast, AMICURE 506 and BF3-400, two competitive commercial latent catalysts, both polymerized within one week.

EXAMPLES 19-22

One Component Epoxy Adhesive/Coating Formulations Containing Latent Catalysts and Dicyandiamide The salt and complexes of Examples 3, 5 and 6 were dispersed at 5 parts (based on active amine equivalent functionality), in 100 parts of EPON 828 epoxy resin, having an EEW (epoxy equivalent weight) of 185 to 190 along with 5 parts of dicyandiamide curing agent and 2.5 parts fumed silicone thixotrope, using a DISPERMAT CV disperser at 2500 rpm for 3 minutes.

Gel times were tested on twenty gram portions of the above mixes in 18 by 150 mm test tubes, using a SUNSHINE gel meter that was equipped with a thermostatically controlled silicone oil bath, as in Examples 7-14.

Table 2 demonstrates the high latency of the dimethylaminopyridine complex of boron trifluoride and salt of 3L-naphthalenesulfonic acid. This is demonstrated by long 100° C. gel times and in FIG. 1. the flat viscosities at 25° C. over a 2 month aged period. Gel times at 100° C. with these salts are quite long, i.e., 813.2 minutes with the BF$_3$ complex and 1384 minutes with the NSA salt version. Both of these compositions show significantly slower 100° C. gel times as compared to two commercially available products included in the evaluation, ANJICURE PN 23 (an amine adduct of epoxy resin) and CUREZOL 2 MA OK (2,4-diamino-612'-methylimidazolyl-(1)'] ethyl-s-triazine isocyanurate adduct). Additionally, the ratio of gel times at 100° and 150° C. is very high for the inventive materials as compared to the commercial offerings. (DMAP-BF$_3$=63.5; DMAP-NSA 144.2; PN23=25.7; 2MATOK=18.4).

EXAMPLE 23

Preparation of Clear Coating Composition

A. Preparation of hydroxy-functional acrylic resin

A hydroxy-functional acrylic resin was prepared as generally described in U.S. Pat. No. 4,871,806 (Example 3). Thus, a polymerization reactor equipped with mechanical stirrer, a water cooled condenser, nitrogen inlet, water trap, thermometer, heating mantel and fluid metering pump was charged with 172.5 parts of n-butyl acetate. The reactor was heated to about 237° F. and a monomer premix composed of 96.2 parts of methyl methacrylate, 63.0 parts of butyl acrylate, 58 parts of hydroxy ethyl methacrylate, 54 parts styrene and an initiator premix composed of 11.5 parts n-butyl acetate and 5.7 parts Vazo 67 was metered simultaneously into the polymerization reactor at a constant rate over about 4 hours. The reaction temperature was maintained for an additional 2 hours after the addition was completed and cooled for one hour. The resulting hydroxy-functional polymer had a number average molecular weight of about 9600.

B. Preparation of carboxy-functional acrylic polymer

A carboxy-functional acrylic polymer was prepared as described in Example 2 of U.S. Pat. No. 4,871,806. Thus, a reactor equipped with mechanical stirrer, reflux condenser, thermometer, nitrogen inlet and fluid metering pump was charged with 1621.2 parts xylene which was then heated to 120° C. under nitrogen. A monomer mixture composed of 1013.2 parts hydroxy ethyl acrylate, 1013.2 parts Tone M-100 (trade name of Union Carbide's hydroxy acrylic/caprolactone adduct believed to be the reaction product of 1 mole of hydroxy ethyl acrylate and 2 moles of caprolactone), 2837.2 parts methyl methacrylate, 3242.1 parts isobutyl methacrylate, 81.1 parts Vazo 67 (trademark for E. I. dupont initiator) and 6352.9 parts xylene was metered into the reaction vessel over a period of 3 hours while maintaining the temperature of the reaction vessel at 120° C. After the monomer mix addition was complexed, the temperature of the reaction mixture was raised to reflux (137° C.) and 20.3 parts Vazo 67 in 131.4 parts xylene was added over a period of 30 minutes. Reflux temperature was maintained for one additional hour. After cooling the reaction mixture to room temperature, 1144.4 parts xylene were added. The polymeric solution was heated to 60° C. and 10.8 parts triethyl amine was added. The reaction mixture was stirred and maintained at 60° C. for about 6 hours. The resulting carboxylic acid-functional acrylic polymer had a theoretical percent solids of 48.1, a Gardner Holdt viscosity of V-, and an acid equivalent weight of 790.

C. Preparation of Anhydride-Functional Acrylic Polymer

An anhydride-functional acrylic polymer was prepared as generally described in U.S. Pat. No. 4,871,806, Example 1. A four neck, round bottom reaction flask equipped with nitrogen inlet, condenser, mechanical stirrer, and fluid metering pump was charged with 1472 parts xylene, 240 parts maleic anhydride and heated to reflux (139° C.) under nitrogen. A monomer mixture of 480 parts isobutyl methacrylate, 720 parts butyl acrylate, 720 parts methyl methacrylate, 120 parts maleic anhydride and 60 parts t-butyl perbenzoate were then metered into the reaction over a 3-hour period. Halfway throughout the addition, an additional 120 pats of maleic anhydride was charged to the reaction vessel and monomer addition was continued. After refluxing the reaction mixture for an additional 15 minutes, 12 parts of t-buty perbenzoate in 1228 parts xylene were added over 45 minutes. Heating was continued for 2 hours at reflux. The resulting xylene soluble anhydride-functional resin was 61.2% solids, had a Gardner Holdt viscosity of about 24.5, an acid value of 116.5, and density of approximately 8.6 pounds per gallon.

D. Preparation of Clear Coating

A clear coating composition Was prepared according to the following formulation.

| Component | Parts by Weight |
|---|---|
| Hydroxy-Functional Acrylic Resin, see Part A | 165.2 |
| Polybutylacrylate[a] | 1.0 |
| 3,4-epoxycyclohexylmethyl 3,4-epoxycyclohexane carboxylate | 55.0 |
| Acid Functional Polymer, see Part B | 424.1 |
| Byk 300[b] | 2.8 |
| Xylene | 38.1 |
| Toluene | 42.0 |
| UV Absorber[c] | 5.0 |
| 20% DMAP-BF$_3$ in Methyl Isobutyl Ketone | 4.5 |
| Anhydride Functional Polymer, See Part C | 39.8 |

[a]56% solution in xylene available from Ford Motor Company as Ch-5967-52
[b]BYK Mallinckrodt Chem. GMBH
[c]Ciba Geigy, Tinuvin 328

The above components were mixed to form a curable composition having exceptional latency/activity characteristics. The composition was applied to iron phosphate treated cold rolled steel substrates and baked for 30 minutes at 250° F. Hardness and MEK rub results are demonstrated in Table 3 below.

TABLE 3

| Hardness/MEK Solvent Rub Results, Baked Coatings | |
|---|---|
| Konig Pendulum Hardness: | |
| 1 Day | 89 |
| 1 Week | 111 |
| 3 Weeks | 113 |
| MEK Rubs | >150 |
| 20 Gloss | 94 |

EXAMPLES 24-28

Preparation of Clear Coatings

A. Preparation of Hydroxy-Functional Acrylic Polymer

For incorporation into a clear coat, a hydroxy-functional acrylic polymer is prepared as described in European Patent Application No. 88119031.8 filed Nov. 15, 1988 (published May 24, 1989, EP 0316874). Accordingly, a four neck, round bottom reaction flask equipped with nitrogen inlet, condenser, mechanical stirrer, and fluid metering pump is charged with methyl amyl ketone (4,000 parts) and heated to reflux. A monomer mix of hydroxy ethyl acrylate (600 parts), butyl acrylate (1,500 parts), styrene (2,100 parts), methyl methacrylate (600 parts), Tone TM M-100 (1,200 parts) (hydroxy-functional acrylic monomer produced by Union Carbide Corporation having a molecular weight of about 344), Vazo-67 (210 parts) (initiator sold by E. I. du Pont believed to be 2,2'-azobis(2-methylbutyronitrile)), parts 3-mercapto propanol (55.6), and a subsequent addition of 64.4 parts 3-mercapto propanol are charged over a period of three hours under a nitrogen blanket while maintaining reflux temperature.

The mixture is maintained at reflux temperature until the resultant resin has a percent solids of approximately 56.4% (94% conversion). The resin is then solvent stripped under vacuum to 80% solids by weight.

B. Preparation of Another Hydroxy-Functional Acrylic Polymer

In a manner similar to part A, another hydroxy-functional acrylic polymer is prepared by charging a reaction vessel with 279.54 parts aromatic naptha heated to about 320° F. A monomer mixture comprising 137.64 parts styrene, 130.54 parts methyl methylacrylate, 196.91 parts butyl acrylate and 186.15 parts hydroxyethyl methacrylate, is charged into the reaction vessel at a uniform rate over about five hours. Simultaneously with the addition of the monomer mixture, a mixture of 28.62 parts t-butyl perbenzoate in 40.60 parts aromatic naptha is also added to the reaction vessel. The reaction mixture is then maintained at about 320° F. for about 90 minutes at which point the resultant resin has a percent solids of approximately 68%.

C. Preparation of Anhydride-Funtional Acrylic Polymer

As also described in the above-noted European Patent Application No. 88119031.8, an anhydride-functional acrylic polymer is prepared by charging 694.4 parts of maleic anhydride and 2777.8 parts of xylene into a four neck reaction flask equipped with a nitrogen inlet, mechanical stirrer, water trap, condenser and fluid metering pump. The mixture is then heated to reflux, and a monomer mixture comprising 2777.8 parts butyl acrylate, 2777.8 parts methyl methacrylate, 694.4 parts maleic anhydride, and 158 parts t-butyl perbenzoate is charged into the reaction flask over a period of three hours under a nitrogen blanket while maintaining reflux temperature. The mixture is maintained at that temperature for about 15 minutes at which point a mixture of 30.9 parts t-butyl perbenzoate in 277.8 parts xylene is charged over a period of 45 minutes. The reaction mixture is then maintained at reflux temperature for about two hours. The resulting anhydride-functional resin is about 71% solids by weight, and has an acid value of about 113.2.

D. Preparation of Second Anhydride-Functional Acrylic Polymer

In like manner to Part C, an anhydride-functional resin comprising 20% maleic anhydride, 20% isobutyl methacrylate, 30% butyl acrylate, and 30% methyl methacrylate is prepared as a 61% solid solution in xylene.

E. Clear Coating Compositions

Clear coating compositions are prepared by admixing anhydride-functional vehicles (AFV), hydroxyl-functional vehicles (HFV) and epoxy-functional vehicles (EFV) according to the following formulations:

| Example | AFV | HFV | EFV | Ratio (AFV/HFV/EFV) |
|---|---|---|---|---|
| 24 | Part C | Part A | ERL 4299* | 2/1/1.25 |
| 25 | Part C | Part A | ERL 4299 | 2/1/1.5 |
| 26 | Part C | Part A | ERL 4299 | 2/1/2 |
| 27 | Part C | Part B | ERL 4299 | 2/1/1.5 |
| 28 | Part D | Part B | ERL 4299 | 1/1/1 |

*bis(3,4-epoxycyclohexylmethyl)adipate from Union Carbide Corporation.

Into each of the coating formulations are blended about 3 parts DMAP-BF$_3$ as prepared in Example 5 (based on anhydride compound solids). The resulting curable formulations again exhibit excellent latency/activity and color characteristics. The formulations are reduced with xylene to an appropriate application viscosity and then spray applied over Bonderite ® 1000 treated steel panels. When thereafter cured by baking at 125° C., quality clear coats are obtained having good hardness, color (e.g. clarity), durability and other desirable properties. Further, these quality clear coats are also obtained over basecoats (e.g. pigmented basecoats) on the substrate, making these clear coating compositions particularly advantageous for application in automobile and like industries.

EXAMPLE 29

Heat-Curable Clear Coating Composition

A heat-curable clear coating composition is prepared generally as described in EP 0411927 (February 1991). The following procedures are thus carried out.
A. Preparation of a Polyanhydride

| Part | Ingredient | Parts By Weight |
|---|---|---|
| 1 | Xylene | 232.10 |
| 2 | Styrene | 91.70 |
|   | Butylmethacrylate | 122.20 |
|   | Butylacrylate | 232.2 |
|   | Xylene | 50.20 |
| 3 | Itaconic acid | 191.60 |
|   | Xylene | 60.00 |
| 4 | 75% Tert-Butylperoxyacetate Initiator ("Lucidol 70" from the Lucidol Division of Penwalt Corporation) | 30.50 |
|   | Propyleneglycolmonomethyletheracatate | 12.10 |
|   | Xylene | 57.50 |
| 5 | Propyleneglycolmonomethyletheracetate | 102.10 |
| 6 | Propyleneglycolmonomethyletheracetate | 102.10 |

Part 1 is added to a reactor equipped with a thermometer, stirrer, dropping funnel, water separator, nitrogen purge and condenser and heated to reflux. Parts 2 and 3 are premixed and added to the reactor over 3 hours simultaneously. Part 4 is premixed and added to the reactor over 3 hours and 20 minutes beginning with the start of Parts 2 and 3. The batch is then maintained at reflux until 25.2 parts of water are collected in the water separater. Part 5 is then added to the batch and 341.3 parts of solvent are removed by distillation. Part 6 is then added to the batch, and it is cooled.

This polymer solution has a Garner-Holdt viscosity of Z1+½ and a measured solids of 69.7%. The anhydride content is about 0.91 Meq/gm and the acid content about 0.19 Meq/gm. The molecular weight as measured by gel permeation chromatography is Mn=2074 and Mw=5093.

B. Preparation of Acid Polymer Component

A butyl acrylate/methacrylic acid copolymer is prepared as follows:
A reactor is charged with the following:

| | |
|---|---|
| Propyleneglycolmonomethyletheracetate (PM acetate) | 1604.0 parts |
| Butyl acetate | 441.0 parts |
| Xylene | 1243.0 parts |

This mixture is heated with agitation under nitrogen to reflux. Then the following mixture is added at a uniform, linear rate over three hours while maintaining reflux.

| | |
|---|---|
| Butyl acrylate monomer | 2427.0 parts |
| Methacrylic acid monomer | 1630.0 parts |
| Tertiary butyl peroxyacetate ("Lucidol 70" from Penwalt) | 224.0 parts |

Then the following mixture is added over ten minutes while maintaining reflux temperature:

| | |
|---|---|
| Xylene | 200.0 parts |
| Tertiary butyl peroxyacetate | 19.0 parts |

The mixture is maintained for one hour at reflux temperature and then diluted with the following:

| | |
|---|---|
| PM Acetate | 692.0 parts |
| Total | 8480.0 parts |

This polymer has a Garner-Holdt viscosity of Z1+½ and a measured solids of 52.3%. The acid content is 2.28 Meq/gm and molecular weight by gel permeation chromatography is Mn=2762, Mw=6108.

A coating composition using DMAP-BF$_3$ catalyst is prepared by thoroughly blending the following constituents:

| | Parts By Weight |
|---|---|
| Polyanhydride (from Part A) | 453.2 |
| PM acetate | 38.2 |
| Methyl hexahydrophthalic anhydride | 57.5 |
| Resiflow S ® (acrylic flow additive from Estron Chemical Co.) | 3.4 |
| Butyl acetate | 118.7 |
| Araldite CY-184 ® (Epoxy resin from Ciba-Geigy) | 238.1 |
| Acid polymer (from Part B) | 174.3 |
| Butanol | 38.8 |
| Tinuvin 292 ® (Ciba-Geigy hindered amine light stabilizer) | 13.2 |
| Tinuvin 1130 (Ciba-Geigy UV screener) | 20.1 |
| 20% DMAP-BF$_3$ in butyl acetate | 58.7 |
| Total | 1196.2 |

The resulting curable coating composition exhibits the advantageous latency/activity, color and other properties noted above.

In testing, the resulting coating composition is reduced to a spray viscosity of 35 seconds measured with a No. 2 Zahn cup accomplished by adding butyl acetate. The coating composition is sprayed onto a primed metal panel coated with a waterborne basecoat and cured at 80° to 165° C. to provide a clear coat having advantageous hardness, color and other desired properties. When sprayed over solvent borne melamine cured basecoat and cured at 110° to 165° C., the resulting clear coating exhibits these same advantageous properties.

EXAMPLE 30

Powder Coating Composition

A. Preparation of Powder Coating
Epon 2002 Solid Epoxy resin (95 parts), dicyandiamide (5 parts) and DMAP-BF$_3$ (0.1 parts) were combined and mixed and pulverized for 10 minutes by mortar and pestal. A 0.9 gram portion of this powder mixture was weighed out onto a 3-inch flat aluminum pan and tested for gel time at 200° C., using the Powder Coatings Institute (PCI) standard test method for gel time. This gel time measured 103 seconds, producing a material of pencil hardness 2H–3H as measured 30 minutes after gel point. Furthermore, this powder coating exhibits superior gel time stability when aged at 40° C. (using the PCI gel time method). It was thus demonstrated that DMAP-BF$_3$ is a highly advantageous catalyst in powdered coating compositions.

What is claimed is:

1. A latent one component heat-curable epoxy resin formulation comprising epoxy resin and a salt or complex selected from the group consisting of:

4-(N,N-dimethylamino)pyridine-p-toluenesulfonic acid addition salt;

4-(N,N-dimethylamino)pyridine-1-naphthalenesulfonic acid addition salt;

4-(4-methyl-1-piperidinyl)pyridine-p-toluenesulfonic acid addition salt;

4-(4-methyl-1-piperidinyl)pyridine-1-naphthalenesulfonic acid addition salt; and 4-(4-methyl-1-piperidinyl)pyridine-boron trifluoride complex.

2. The formulation of claim 1 which also comprises a dicyandiamide, acid anhydride, or adipic dihydrazide curing agent.

3. A process for forming a cured epoxy resin material at temperatures and cure times suitable for a production line scale operation, comprising heating an epoxy resin having blended therein a curing agent and as accelerator about 1 to 8 parts by weight of 4-(N,N-dimethylamino)pyridine-boron trifluoride complex per 100 parts by weight epoxy resin at a temperature of about 100° to 150° C. and for a period of about 5 to 90 minutes.

4. The process of claim 3 wherein the curing agent is a dicyandiamide, acid anhydride or adipic dihydrazide curing agent.

5. A heat-curable coating composition, comprising:

(i) a compound having anhydride functionality;

(ii) a compound having epoxy or hydroxyl functionality;

with the proviso that at least one of (i) or (ii) has acrylic functionality; and (iii) as a crosslinking catalyst, 4-(N,N-dimethylamino)pyridine-boron trifluoride complex.

6. The composition of claim 5 wherein the compound having anhydride functionality is an acrylic-anhydride copolymer prepared from one or more of the monomers of methacrylates or acrylates with one or more of the monomers of itaconic acid, itaconic anhydride, maleic anhydride, maleic acid or isobutenyl succinic anhydride.

7. The coating composition of claim 5 in which (ii) includes a hydroxyl-functional compound.

8. The coating composition of claim 7 wherein the hydroxyl-functional compound has acrylic functionality.

9. The coating composition of claim 8 wherein the hydroxyl-functional compound is a hydroxy-functional acrylic resin.

10. The coating composition of claim 5 in which (ii) includes an epoxy-functional compound.

11. The coating composition of claim 10 wherein the epoxy-functional compound has acrylic functionality.

12. The coating composition of claim 5 which includes an acid-functional compound.

13. The coating composition of claim 10 in which the acid-functional compound is an acid-functional polymer.

14. The coating composition of claim 5 which includes an anhydride-functional compound, an epoxy-functional compound and a hydroxyl-functional compound.

15. The coating composition of claim 14 in which the anhydride-functional compound has acrylic functionality.

16. The coating composition of claim 15 in which the hydroxyl-functional compound has acrylic functionality.

* * * * *

UNITED STATES PATENT AND TRADEMARK OFFICE
CERTIFICATE OF CORRECTION

PATENT NO. : 5,420,223
DATED : May 30, 1995
INVENTOR(S) : John R. Johnson

It is certified that error appears in the above-indentified patent and that said Letters Patent is hereby corrected as shown below:

In column 1, line 66, delete the hyphen between "included" and "some" and insert in lieu thereof a space.

In column 2, line 22, delete "imp, roved" and insert in lieu thereof --improved--.

In column 2, line 28, delete "tile" and insert in lieu thereof --the--.

In column 3, line 19, delete "Hill" and insert in lieu thereof --will--.

Signed and Sealed this

Thirty-first Day of October 1995

Attest:

BRUCE LEHMAN

Attesting Officer

Commissioner of Patents and Trademarks